United States Patent [19]

Willert et al.

[11] Patent Number: 5,035,714
[45] Date of Patent: Jul. 30, 1991

[54] REINFORCEMENT FOR A BONE CEMENT BED

[75] Inventors: Hans-Georg Willert, Göttingen, Fed. Rep. of Germany; Rudolf Koch, Berlingen; Maxa Burgi, Pfyn, both of Switzerland

[73] Assignee: Sulzer Brothers Limited, Winterthur, Switzerland

[21] Appl. No.: 552,780

[22] Filed: Jul. 16, 1990

[30] Foreign Application Priority Data

Jul. 18, 1989 [CH] Switzerland .................. 2682/89-9

[51] Int. Cl.⁵ .......................... A61F 2/28; A61F 2/36
[52] U.S. Cl. .......................... 623/16; 623/23
[58] Field of Search .............. 623/16, 16 A, 18–23

[56] References Cited

U.S. PATENT DOCUMENTS

| | | | |
|---|---|---|---|
| 3,710,789 | 1/1973 | Ersek | 623/16 X |
| 4,064,567 | 12/1977 | Burnstein et al. | 623/18 |
| 4,718,909 | 1/1988 | Brown | 623/16 |
| 4,888,024 | 12/1989 | Powlan | 623/16 X |
| 4,936,859 | 6/1990 | Morscher et al. | 623/16 X |

FOREIGN PATENT DOCUMENTS

| | | |
|---|---|---|
| 0224890 | 6/1987 | European Pat. Off. |
| 2412304 | 7/1979 | France |
| 2610824 | 8/1988 | France |
| 1525667 | 9/1978 | United Kingdom |

Primary Examiner—Ronald Frinks
Attorney, Agent, or Firm—Kenyon & Kenyon

[57] ABSTRACT

The reinforcement for the proximal region of a bone cement bed for a femoral head prosthesis includes a grid of crossing members at least some of which are wavy. The wavy members have a high wavy shape lengthwise and spring in as the gap between a bone cavity and a prosthesis stem narrows. The prosthesis is fixed by averaging out of the restoring forces and the gap size mechanically until the bone cement has cured.

17 Claims, 4 Drawing Sheets

REINFORCEMENT FOR A BONE CEMENT BED

This invention relates to a reinforcement for a bone cement bed. More particularly, this invention relates to a reinforcement for the proximal region of a bone cement bed for a femoral head prosthesis.

As is known, various types of elements have been used for the mounting of a femoral head prosthesis in a bone. For example, French Patent 2610824 describes the use of a pair of leaf spring-like members on a proximal zone of a prosthesis for engaging within a bone cavity. U.S. Pat. No. 4,718,909 describes the use of spacers, for example, spring-like spacing sleeves, for the implanting a femoral head prosthesis in place. Still further, it has been known from British Patent 1,525,667 and European Patent application 0224890 to employ mesh or spring-like elements for implants in bones. Generally, these types of structures have not been used for reinforcing a bone cement bed but rather for positioning and holding a prosthesis in place.

On the other hand, it has been known from French Patent 2,412,304 to provide a reinforcement which is drawn like a sock over a stem of a femoral head prosthesis for reinforcing a bone cement bed. In this case, the reinforcement is placed on the stem of the prosthesis and pressed together with the stem into a cement bed which has been previously introduced into a bone cavity. This reinforcement is intended to provide for subsequent strengthening and forms a weave-like texture around which the still flowable bone cement flows against the direction of introduction of the prosthesis. However, one disadvantage of this is that there is a repeated cutting of the rising bone cement over its whole length. This leads to the possibility of subsequent cracking in the converging surfaces. Also, there is usually uncertainty about the position of the prosthesis in the cement bed and about distribution of the cement until the cement has set and cured.

Accordingly, it is an object of the invention to ensure the integrity of a bone cement bed in which a reinforcement is implanted.

It is another object of the invention to provide for a uniform distribution of bone cement in a bed in which a reinforcement mesh is implanted.

Briefly, the invention provides a reinforcement for a bone cement bed which is comprised of a plurality of longitudinally disposed wavy members each of which has a crest height corresponding to a multiple of the thickness thereof. In addition, the reinforcement has a plurality of transversely disposed crossing members secured to the wavy members at longitudinally spaced points, corresponding to a length of at least two half-waves of a respective wavy member.

The reinforcement is constructed so as to be placed into a bone cavity prior to introduction of a bone cement.

In one embodiment, the point at which the crossing members are secured to the wavy members are spaced apart a distance equal to at least four half-waves of a respective wavy member while the wavy members are widely spaced from each other so as to form a lattice or grid of large openings. Further, the crest height of each wavy member may be at least three times the thickness of the wavy member.

In another embodiment, the reinforcement is formed of a plurality of longitudinally disposed wavy members which are connected at intermediate points to each other in order to define a diamond shaped grid. Again, each member has a crest height corresponding to a multiple of the thickness. In addition, a crossing member is disposed at a proximal end of the wavy members and is secured to each wavy member thereat while a second crossing member is disposed at and is secured to a distal end of the wavy members.

In still another embodiment, the reinforcement is formed of a plurality of interconnected members which define a flat diamond shaped grid with a plurality of intersections and a plurality of deformable elements each of which is secured to the grid at a point intersection thereof. Further, each deformable element includes a plurality of wavy members which project radially from a respective point of intersection away from the grid. For example, where the grid defines a tubular envelope for receiving an implant, the wavy members project inwardly of the envelope to resiliently abut the implant.

In still another embodiment, the reinforcement is comprised of a plurality of longitudinally disposed wavy members each of which is secured to one adjacent member at spaced apart points so as to define a grid. In addition, each member has an unsupported bent portion between each pair of connecting points. This bent portion is further angularly disposed relative to the grid and is resiliently deformable therefrom. For example, where the grid defines a tubular envelope for receiving an implant, the bent portions project inwardly of the envelope in order to resiliently abut the implant.

With the various reinforcements, the position of a prosthesis can be prefixed before the curing of a bone cement. In this respect, the gap between the prosthesis and the bone can be averaged out automatically by an averaging-out of the restoring forces relative to the prosthesis. Also, the position of the prosthesis can be checked, and as the prosthesis is pushed in further, altered.

These and other objects and advantages of the invention will become more apparent from the following detailed description taken in conjunction with the accompanying drawings wherein.

Figure 1:
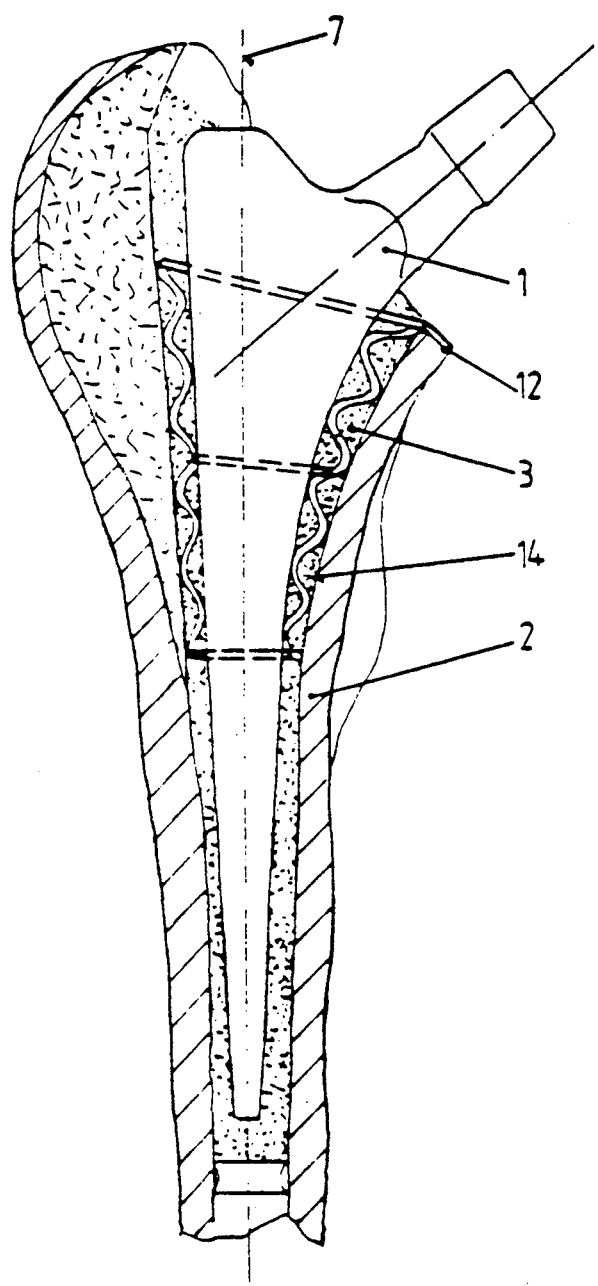
FIG. 1 illustrates a diagramatic view in side elevation of a vertical section through a proximal part of a femur bone having an implanted stem and having a reinforcement in accordance with the invention.

Referring to FIG. 1, a femoral prosthesis 1 is implanted in a femur bone 2 by means of a bone cement bed 3. In addition, a reinforcement 4 is provided between the prosthesis 1 and the bone 2 for positioning the prosthesis 1 in place as well as for strengthening the bone cement bed 3. As indicated, the reinforcement 4 is provided in the proximal region of the bone cement bed 3.

Figure 3:
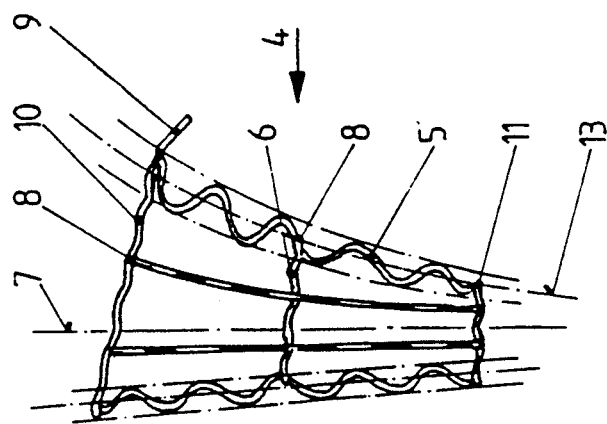
FIG. 3 illustrates a view taken on line III—III of FIG. 2.
Figure 2:
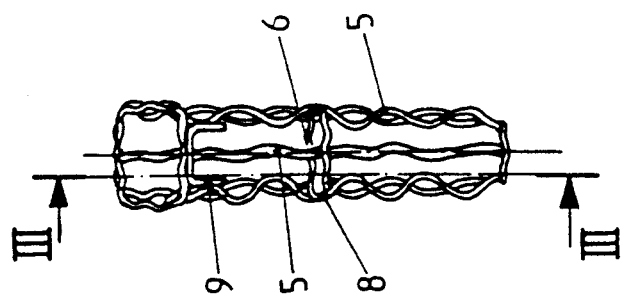
FIG. 2 illustrates a side view of the reinforcement of FIG. 1 prior to implantation.

Referring to FIGS. 2 and 3, the reinforcement 4 is constructed of a plurality of longitudinally disposed wavy members 5 each of which, as shown in FIG. 3, has a crest height corresponding to a multiple of the thickness thereon. For example, the crest height is at least three times the thickness of the member 6. Further, as indicated in FIG. 3, the crest height decreases from the proximal end of the reinforcement 4 towards the distal end.

The reinforcement 4 also has a plurality of transversely disposed crossing members 6 secured to the wavy members 5 at longitudinally spaced points 8 corresponding to a length of at least two half-waves of a respective wavy member 6. As indicated in FIG. 3, the crossing member 6 are spaced apart a distance equal to at least four half-waves of a wavy member 5. Further, each crossing member 6 is secured to a wavy member 5 on the center line 13 (see FIG. 3) of the respective wavy member 5.

As also indicated in FIGS. 2 and 3, the wavy members 5 are disposed in circumferential relation about a longitudinal axis 7 which corresponds to the axis of the prosthesis 1 shown in FIG. 1.

As also shown in FIG. 3, the wavy members 5 are widely spaced apart to form a lattice-like structure.

The reinforcement 4 is also provided with outwardly directed supports 9 which extend from at least one of the wavy members 5 and the crossing member 6 at a proximal end of the reinforcement for abutting a bone. As indicated in FIG. 1, the supports 9 abut against the edge 12 of the femur 2.

Referring to FIG. 1, the outer envelope ends of the reinforcement 4 correspond to the narrowing cavity 14 in the proximal zone of the femur bone. In this respect, the reinforcement is introduced into the cavity 14 before the introduction of bone cement and engages by way of the supports 9 with the bone edge 12. As the prosthesis 1 is introduced, the wavy members 5 engage in the very narrow gaps between the prosthesis stem and the cavity 14 and offer a resistance. As the stem is pushed further into the bone, the wavy members 5 which are the first to bear on both sides flatten until substantially all the members intended for this purpose are in a support situation in accordance with the narrowing of the gap.

Upon implantation, the prosthesis 1 takes up a position in accordance with the equalization of forces between the restoring forces of the carrying wavy members. The prosthesis 1 which has been introduced in the direction of the axis 7 is thus fixed lengthwise and against rotation by a self-locking effect of the friction forces. In addition, the position of the prosthesis may be altered after checking by being pushed in further. Depending upon the force equalization effective on the prosthesis stem, the gap between the stem and the bone cavity 14 is averaged out by the wavy members 5. There are, therefore, virtually no substantial accumulations of bone cement in the gap and there is less build-up of heat during curing, two factors which increase the temperature of the bone cavity.

During the introduction of the prosthesis 1, the wavy longitudinal members 5 are flattened and elongated within the unsupported lengths between the connecting points 8. The crossing member 6 at the top edge 10 and the bottom edge 11 are disposed near or at the center line of the wavy shape and have a reduced crest height to insure that when the reinforcement is pushed in, these crossing members 6 do not engage the cavity 14 so that there is sufficient clearance for a widening by the prosthesis stem which is of conical shape.

As indicated in FIG. 3, each wavy member 5 may be of sine-shape. Further, the unsupported deformable length of each wavy member between the crossing members 6 permits a decrease of the crest height after implanting in a bone and during implantation of the prosthesis.

Figure 4:
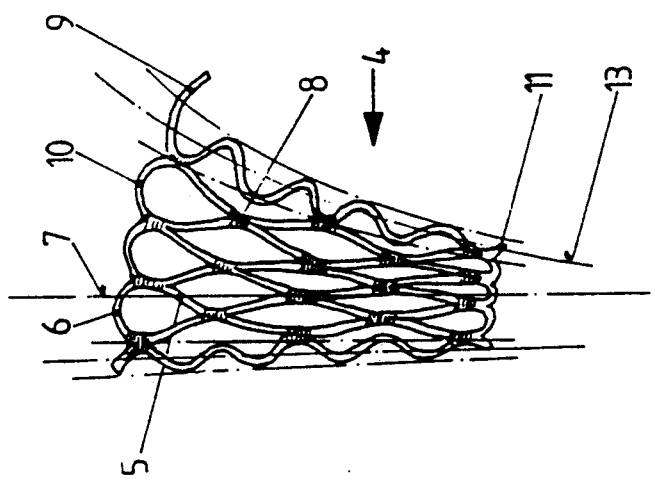
FIG. 4 illustrates a vertical sectional view of a modified reinforcement having a diamond shaped grip in accordance with the invention.

Referring to FIG. 4, wherein like reference characters indicate like parts as above, the reinforcement 4 is formed of a plurality of longitudinally disclosed wavy members 5 which are connected at intermediate points to each other to define a diamond shaped grid. In addition, each member 5 has a crest height corresponding to a multiple of the thickness thereof. As above, the crest height of each wavy member 5 decreases in the distal direction.

In addition, a crossing member 6 is disposed at the proximal end 10 of the wavy members 5 and is secured thereafter while a second crossing member 6 is disposed at the distal end 11 of the wavy members and secured thereat. As indicated, each crossing member is disposed on a center line 13 of a respective wavy member 5.

The advantage of this arrangement is that the reinforcement can be widened over a considerable range transversely. Thus, a single reinforcement can be used for different stem sizes and stem shapes.

Figure 6:
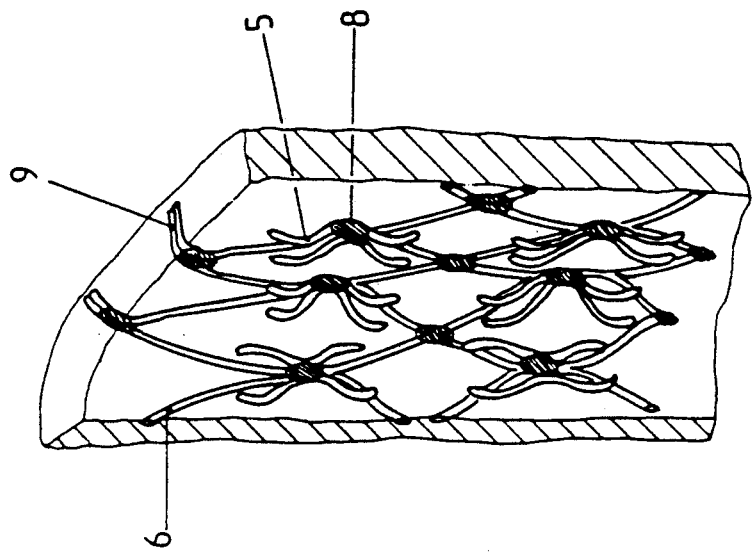
FIG. 6 illustrates a part perspective view of the reinforcement of FIG. 5 having inwardly directed deformable elements in accordance with the invention.
Figure 5:
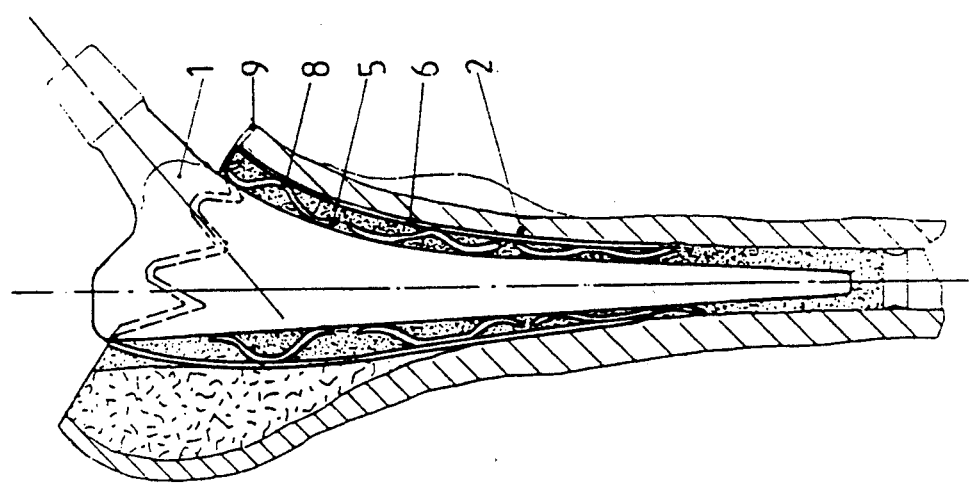
FIG. 5 illustrates a view similar to FIG. 1 of a modified reinforcement constructed in accordance with the invention.

Referring to FIGS. 5 and 6, wherein like reference characters indicate like parts as above, the reinforcement can be constructed of a plurality of interconnected members 6 which are secured together at a plurality of intersections 8 to define a flat diamond shaped grid as well as a plurality of deformable elements secured to the grid at the points of intersection 8. As indicated, each deformable element includes a plurality of wavy members 5 which project from the respective point of intersection 8 away from the grid. Where the grid defines a tubular envelope for receiving an implant, the wavy members 5 project inwardly of the envelope to resiliently abut the implant 1 as indicated in FIG. 5.

In this embodiment, the wavy members are interrupted and are self-aligning on the stem surface of the prosthesis 1 in the manner of tetrapods suspended on a back.

As above, the diamond shaped grid formed by the interconnected members 6 permits ready adaptation to different stem shapes.

Figure 9:
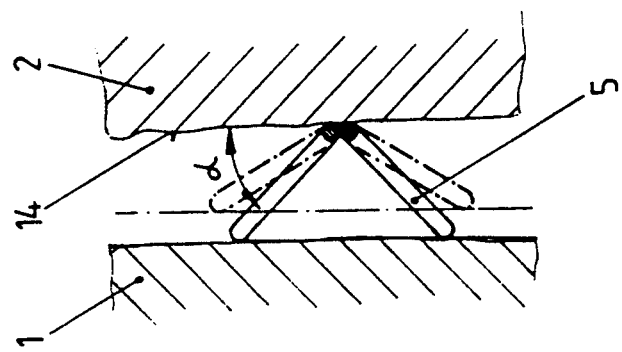
FIG. 9 illustrates a view taken on line IX—IX of FIG. 7.
Figure 8:
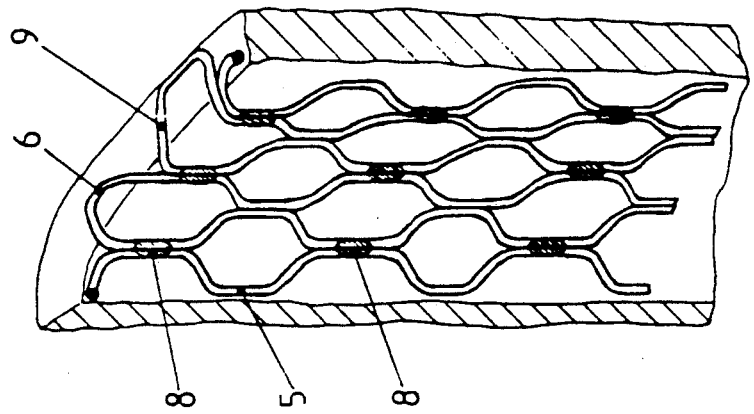
FIG. 8 illustrates a part perspective view of the reinforcement of FIG. 7.
Figure 7:
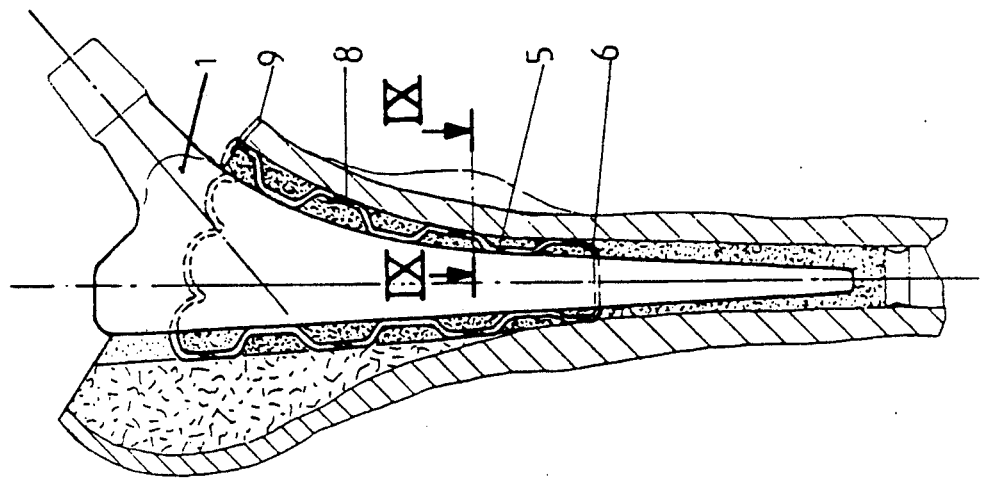
FIG. 7 illustrates a view similar to FIG. 1 of a further modified reinforcement in accordance with the invention.

Referring to FIGS. 7 to 9, the reinforcement is constructed of a plurality of longitudinally disposed wavy members each of which is secured to one adjacent member at spaced apart points 8 to define a grid. In this respect, each pair of members 5 comprise a wavy symmetrical double member. Each member 5 also has an unsupported bent portion between each pair of points of intersection 8, for example of a trapezoidal shape. Each bent portion is also angularly disposed relative to the grid as indicated in FIG. 9 and is resiliently deformable relative to the grid. As indicated in FIG. 9, each bent portion is disposed at an angle α of 50° relative to the grid and has a crest height corresponding to a multiple of the thickness thereof.

When the prosthesis 1 is being implanted into the reinforcement, the bent portions of the wavy members 5 spring away laterally and reduce the angle α but without elongation of the grid and without alteration of the support positions in the bone cavity 14 (see FIG. 9).

The invention thus provides a reinforcement which solves the problem of determining prosthesis position mechanically at introduction of the prosthesis and of reducing heating of a cement during curing, a process associated with an evolution of heat.

What is claimed is:

1. A reinforcement for a bone cement bed comprising a plurality of longitudinally disposed wavy members, each said member having a crest height corresponding to a multiple of the thickness thereof; and a plurality of transversely disposed crossing members secured to said wavy members at longitudinally spaced points corresponding to a length of at least two half-waves of a respective wavy member.

2. A reinforcement as set forth in claim 1 wherein said points are spaced apart a distance equal to at least four half-waves of a respective wavy member.

3. A reinforcement as set forth in claim 2 wherein said longitudinally disposed members are disposed in circumferential relation about a longitudinal axis.

4. A reinforcement as set forth in claim 1 wherein said crest height is at least three times said thickness.

5. A reinforcement as set forth in claim 1 which further comprises outwardly directed supports extending from at least one of said wavy members and said crossing members at a proximal end of the reinforcement for abutting a bone.

6. A reinforcement as set forth in claim 1 wherein each crossing member is disposed on a center-line of each wavy member thereat.

7. A reinforcement as set forth in claim 1 wherein each wavy member has an unsupported deformable length between each pair of crossing members to permit a decrease of the crest height thereof after implanting in a bone and during implantation of an implant thereon.

8. A reinforcement as set forth in claim 1 wherein each wavy member is of sine-shape and has a decreasing crest height from a proximal end to a distal end thereof.

9. A reinforcement for a bone cement bed comprising a plurality of longitudinally disposed wavy members connected at intermediate points to each other to define a diamond shaped grid, each said member having a crest height corresponding to a multiple of the thickness thereof;
a first crossing member at a proximal end of said wavy members secured to each said wavy member thereat; and
a second crossing member at a distal end of said wavy members secured to each wavy member thereat.

10. A reinforcement as set forth in claim 9 wherein said longitudinally disposed members are disposed in circumferential relation about a longitudinal axis.

11. A reinforcement as set forth in claim 9 wherein each crossing member is disposed on a center line of each respective wavy member.

12. A reinforcement for a bone cement bed comprising
a plurality of interconnected members defining a flat diamond shaped grid, with a plurality of intersections; and
a plurality of deformable elements, each said element being secured to said grid at a point of intersection thereof and including a plurality of wavy members projecting radially from a respective point of intersection away from said grid.

13. A reinforcement as set forth in claim 12 wherein said grid defines a tubular envelope for receiving an implant and said wavy members project inwardly of said envelope to resiliently abut the implant.

14. A reinforcement for a bone cement bed comprising a plurality of longitudinally disposed wavy members, each said member being secured to one adjacent member at spaced apart points to define a grid and having an unsupported bent portion between each pair of said points, each said bent portion being angularly disposed relative to said grid and being resiliently deformable therefrom.

15. A reinforcement as set forth in claim 14 wherein said grid defines a tubular envelope for receiving an implant and each said bent portion projects inwardly of said envelope to resiliently abut the implant.

16. A reinforcement as set forth in claim 14 wherein each bent portion is disposed at an angle of 50 degrees relative to said grid.

17. A reinforcement as set forth in claim 14 wherein each bent portion has a crest height corresponding to a multiple of the thickness thereof.

* * * * *